United States Patent [19]

Takenaka et al.

[11] Patent Number: 4,538,609
[45] Date of Patent: Sep. 3, 1985

[54] MANIPULATOR FOR LASER KNIFE

[75] Inventors: Shinya Takenaka; Katsuyoshi Sunago, both of Osaka, Japan

[73] Assignee: Sumitomo Electric Industries, Ltd., Osaka, Japan

[21] Appl. No.: 396,174

[22] Filed: Jul. 7, 1982

[30] Foreign Application Priority Data

Jul. 7, 1981 [JP] Japan ............... 56-105077

[51] Int. Cl.³ ............... A61B 17/36; G02B 5/14
[52] U.S. Cl. ............... 128/303.1; 128/395; 350/96.2; 433/126
[58] Field of Search ............... 128/303.1, 395; 433/126–127; 350/96.32, 96.23, 1.1, 96.15, 96.18, 96.20, 96.21

[56] References Cited

U.S. PATENT DOCUMENTS

| 624,392 | 5/1899 | Smith | 350/96.2 |
|---|---|---|---|
| 3,467,098 | 9/1969 | Ayres | 128/303.1 |
| 3,483,869 | 12/1969 | Hayhurst | 128/303.1 |
| 3,622,743 | 11/1971 | Muncheryan | 128/303.1 |
| 3,851,984 | 12/1974 | Crippa | 433/127 |
| 3,912,364 | 10/1975 | Hudson | 350/96.18 |
| 4,087,158 | 5/1978 | Lewis et al. | 350/96.21 |
| 4,266,547 | 5/1981 | Komiya | 128/303.1 |
| 4,266,549 | 5/1981 | Kimura | 128/303.1 |
| 4,270,845 | 6/1981 | Takizawa et al. | 128/303.1 |
| 4,273,109 | 6/1981 | Enderby | 128/303.1 |
| 4,291,941 | 9/1981 | Melzer | 350/96.21 |
| 4,317,615 | 3/1982 | Herold | 433/126 |

FOREIGN PATENT DOCUMENTS 1041610 10/1978 Canada ............... 128/303.1

Primary Examiner—John D. Yasko
Assistant Examiner—Gene B. Kartchner
Attorney, Agent, or Firm—Sughrue, Mion, Zinn, Macpeak, and Seas

[57] ABSTRACT

A laser knife is provided with a mechanism by which a plurality of specialized hand pieces may be detachably coupled to the front end portion of the optical fiber light path for the laser.

8 Claims, 4 Drawing Figures

MANIPULATOR FOR LASER KNIFE

BACKGROUND OF THE INVENTION

This invention relates to an improvement in a manipulator for a laser knife which uses an optical fiber as a light conducting path.

Laser beams are monochromatic and are excellent in directivity. When a laser beam is focused at a minute point, great energy can be locally obtained. Therefore, laser beams are utilized as laser knifes in the field of medical treatment, and especially when a limited part of the body is subjected to such medical treatment or surgical operation, the use of the laser knife is quite effective.

With a laser knife, a laser beam from a laser oscillating section is applied to that part of the body which is to be subjected to the medical treatment or surgical operation. In this operation, it is required that the laser beam be correctly applied to an extremely small target. In order to meet this requirement, an optical fiber of small weight and excellent flexibility is frequently used as the light conducting path.

In most laser knife manipulators using optical fibers as light conducting paths, the laser beam is applied to the part to be irradiated, with the cover 2 of the optical fiber 1 gripped directly, as shown in FIG. 1, which is an explanatory diagram of the front end portion of a manipulator. Accordingly, the optical fiber 1 is liable to bend during irradiation, as a result of which it is impossible to correctly apply the laser beam to the body part to be irradiated, and the temperature of the manipulator is increased by the reflected light.

In order to overcome these drawbacks, a laser knife manipulator has been proposed in the art, in which, as shown in FIG. 2, the front end portion of the optical fiber 1 is inserted into a hand piece 3 which is made of a straight pipe of metal or synthetic resin. However, this conventional manipulator still suffers from drawbacks in that it is difficult to apply the laser beam in directions other than the axial direction of the hand piece 3; i.e., sometimes the target cannot be lined up with the hand piece and irradiated with the laser beam, with the result that the range of application of the device in medical treatments or surgical operations is limited.

SUMMARY OF THE INVENTION

Accordingly, an object of this invention is to eliminate the above-described drawbacks accompanying a conventional laser knife manipulator.

More specifically, an object of the invention is to provide a laser knife manipulator with which a laser beam can be correctly applied to all parts to be irradiated irrespective of the positions and the configurations of such parts.

The foregoing object and other objects as well as the characteristic features of the invention will become more apparent from the following detailed description, when read in conjunction with the accompanying drawings, in which like parts are designated by like reference numerals.

DETAILED DESCRIPTION OF THE PREFERRED EMBODIMENTS

Figure 1:
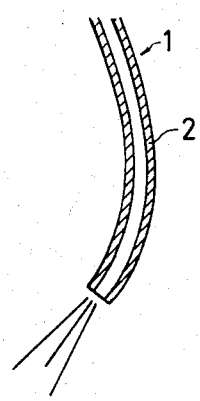
FIG. 1 is a longitudinal sectional view of the emergent end portion of an example of a conventional laser knife manipulator.
Figure 2:
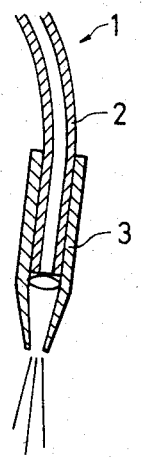
FIG. 2 is a longitudinal sectional view of the end portion of another example of the conventional laser knife manipulator.
Figure 3:
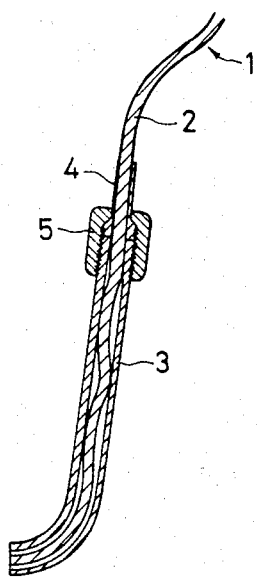
FIG. 3 is a longitudinal sectional view of the end portion of an example of a laser knife manipulator according to this invention; and, FIG. 4 is a longitudinal sectional view of the end portion of another example of a laser knife manipulator according to the invention.

A first example of a laser knife manipulator according to this invention, as shown in FIG. 3, includes an optical fiber 1 as a light conducting path adapted to conduct the laser beam from a laser oscillating section (not shown); and a hand piece 3 detachably disposed over the end portion of the optical fiber 1. The hand piece 3 is suitably shaped according to the configuration and the position of the part to be irradiated with the laser beam. More specifically, the hand piece 3 is made of a metal or synthetic resin and has an inside diameter which is slightly larger than the outside diameter of the cover 2 of the optical fiber. One end portion of the hand piece 3 is bent as shown in FIG. 3. Male threads are formed on the outer wall of the other end portion of the hand piece. The manipulator further includes a rubber sleeve 4 having an O-ring-shaped protrusion at one end; and a cap 5 having female threads on the inner wall thereof. The rubber sleeve 4 is positioned over the optical fiber cover 2 in such a manner that the rubber sleeve 4 is adjacent the hand piece 3, and is held there by its own elastic force. Under this condition, the cap 5 is screwed onto the threaded portion of the hand piece.

In other words, first the cap 5 and the rubber sleeve 4 are placed over the optical fiber cover 2, and then the optical fiber 1 is inserted into the hand piece 3. Under this condition, the cap 5 is screwed on the threaded portion of the hand piece 3. As a result, the O-ring-shaped protrusion of the rubber sleeve 4 is pressed against the hand piece 3, so that the hand piece 3 is fixedly secured to the cover 2.

It goes without saying that the hand piece 3 can be readily removed from the optical fiber 1 by unscrewing the cap 5.

A variety of hand pieces such as straight hand pieces and bent hand pieces of different radii of curvature can be fabricated separately according to the configuration and the position of the body parts to be irradiated. Accordingly, with a suitable hand piece, the laser beam can be applied correctly to the desired location, and the target to be irradiated will never be obscured by the operator's hand.

If the hand piece 3, the rubber sleeve 4 and the cap 5 are removed from the optical fiber 1, then the latter can be readily inserted into the laser knife insertion hole of a conventional endoscope, so that it can be used with such an endoscope.

Figure 4:
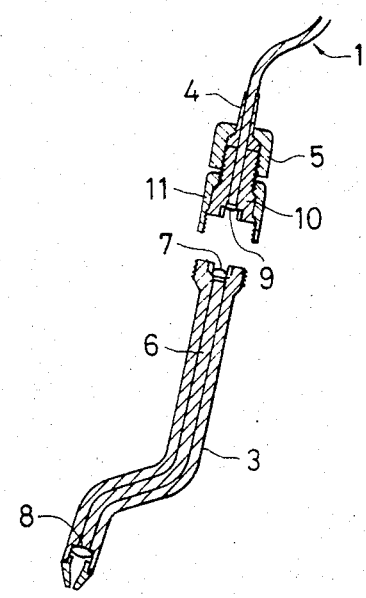

Another example of a laser knife manipulator according to the invention is as shown in FIG. 4. In this example, an optical fiber 6 is fixedly inserted into a hand piece 3 which has been shaped as desired, and when the hand piece 3 is secured to an optical fiber 1, the latter is optically coupled to the optical fiber 6.

For this purpose, a coupling lens 7 is fixedly secured to the coupling end of the optical fiber 6 in the hand piece 3. In this example, lens 8 for condensing the laser beam is fixed to the other end of the optical fiber 6 in the hand piece 3. Similarly as in the first example shown in FIG. 3, a rubber sleeve 4 and a cap 5 are placed over the optical fiber 1 which is to be coupled to the hand piece 3. A lens holder 10 holds a coupling lens 9 which is set at the front end of the optical fiber 1. The lends holder 10 is threadably engaged with the cap 5. A coupling nut 11 is provided on the lens holder 10. The coupling nut 11 is used to fixedly couple the lens holder 10 to the hand piece 3.

First, the front end portion of the optical fiber 1, on which the rubber sleeve 4 and the cap 5 have been mounted, is inserted into the lens holder 10. Then, the cap 5 is screwed on the lens holder 10, so that the latter 10 is fixedly secured to the front end portion of the optical fiber. Then, the coupling nut 11 is tightened so that the hand piece 3 with the optical fiber 6 is fixedly secured to the lens holder 10. As a result, the optical fiber 1 is optically coupled to the optical fiber 6, and the hand piece 3 is fixedly secured.

In the second example described above, two lenses are used for optical coupling; however, the number of lenses may be one or more than two.

As is apparent from the above description, a number of hand pieces which are shaped as desired according to the configuration of the body part to be irradiated with the laser beam can be selectively and readily used. Therefore, the laser beam can be correctly applied to that part which is to be irradiated. Furthermore, the invention makes it possible for one laser knife to perform dental and oral surgical operations, as well as surgical operations in other fields. In addition, the laser knife manipulator can be readily coupled to an endoscope. Thus, the laser knife manipulator according to the invention has a wide range of application.

What is claimed is:

1. A manipulator for a laser knife using an optical fiber light guide as a light conducting path, comprising;
    an elongated hand piece detachably coupled to a forward portion of said optical fiber light guide, said hand piece being shaped to enable the part to be irradiated with said laser to be confronted with an end portion of said hand piece,
    an elastic sleeve member comprising a continuous member positioned with a thickened portion abutting the opposite end portion of said hand piece, and being held to said fiber light guide under its own elastic force, and a connector disposed over said optical fiber light guide and said thickened portion of said elastic sleeve and adapted to couple said hand piece to said fiber light guide through said thickened portion of said elastic sleeve disposed between said connector and said fiber light guide, by pressing said thickened portion into close contact with said fiber light guide and said hand piece.

2. An apparatus as claimed in claim 1, said connector and said hand piece each having connection means for engaging one another.

3. An apparatus as claimed in claim 2, said connection means comprising mating screw threads.

4. An apparatus as claimed in claim 1, said hand piece receiving said forward portion of said optical fiber internally thereof.

5. An apparatus as claimed in claim 1, said hand piece including a further optical fiber light guide fixedly received therein, said manipulator further including means for optically coupling said forward portion of said optical fiber light guide and said further optical fiber light guide of said hand piece.

6. An apparatus as claimed in claim 5, said optical coupling means comprising at least one lens disposed in at least one of said hand piece and said connector-coupler.

7. An apparatus as claimed in claim 5, said connector-coupler including a lens holder and a coupling member for connecting said lens holder to said hand piece, and said connector comprising a cap member coupling said lens holder and said forward portion of said optical fiber light guide.

8. A manipulator for a laser knife using an optical fiber light guide as a light conducting path, comprising;
    an elongated hand piece detachably coupled to a forward portion of said optical fiber light guide, said hand piece being shaped to enable the part to be irradiated with said laser to be confronted with an end portion of said hand piece,
    an elastic sleeve member positioned over a part of said fiber light guide and being held to said fiber light guide under its own elastic force,
    a connector disposed over said optical fiber light guide and said elastic sleeve,
    a connector-coupler detachably connected to both said connector and said hand piece and having an end adjacent said elastic sleeve member, said connector coupling said connector-coupler to said fiber light guide through a portion of said elastic sleeve disposed in contact with each of said coupler, said connector-coupler and said fiber light guide.

* * * * *